United States Patent [19]

Winefordner et al.

[11] Patent Number: 4,942,134
[45] Date of Patent: Jul. 17, 1990

[54] METHOD AND APPARATUS FOR SCIENTIFIC ANALYSIS UNDER LOW TEMPERATURE VACUUM CONDITIONS

[75] Inventors: James D. Winefordner; Bradley T. Jones, both of Gainesville, Fla.

[73] Assignee: The University of Florida, Gainesville, Fla.

[21] Appl. No.: 157,788

[22] Filed: Feb. 19, 1988

[51] Int. Cl.$^5$ .................. G01N 1/00; G01N 21/00; G01N 30/62

[52] U.S. Cl. .................... 436/161; 250/338.1; 250/341; 250/352; 356/244; 356/326; 356/426; 422/70; 422/83; 422/89; 422/82.05; 436/164; 436/166; 436/171

[58] Field of Search .............. 422/68, 89, 83; 436/36, 436/161, 164, 171, 166, 147; 250/338.1, 341, 352; 356/326, 426, 244

[56] References Cited

U.S. PATENT DOCUMENTS

| | | | |
|---|---|---|---|
| 4,158,772 | 6/1979 | Reedy | 356/244 |
| 4,495,414 | 1/1985 | Barrie et al. | |
| 4,594,226 | 6/1986 | Reedy | |
| 4,600,559 | 7/1986 | Hiatt | |

OTHER PUBLICATIONS

Kirkbright, G. F. & C. G. De Lima, The Detection and Determination of Polynuclear Aromatic Hydrocarbons by Luminescence Spectrometry Utilixing the Shpol'skii Effect at 77 K, Analyst, Jun., 1974, vol. 99, pp. 338–354.

Inman, E. L., Jr., A. Jurgensen & J. D. Winefordner, Analytical Figures of Merit for Low-Temperature Luminescence of Polynuclear Aromatic Compounds, Analyst, May, 1982, vol. 107, pp. 538–543.

Lai, E. Q., E. L. Inmar, Jr., & J. D. Winefordner, Conventional Fluorescence Spectrometry of Polynuclear Aromatic Hydrocarbons in Shpol'skii Matrices at 77 K*, Talanta, vol. 29, pp. 601–608, 1982.

Colmsjo, Anders & Ulf Stenberg, Identification of Polynuclear Hydrocarbons by Shpol'skii Low Temperature Fluorescence, Analytical Chemistry, vol. 51, p. 145, Jan. 1979.

Ward, J. L., R. P. Bateh & J. D. Winefordner, Evaluation of an Effective Conduction Cooling Device for Low-Temperature Phosphorimetry, Applied Spectroscopy, vol. 34, No. 1, 1980, pp. 15–17.

Ward, J. L., G. L. Walden, R. P. Bateh & J. D. Winefordner, A New, More Efficient Conduction Cooling Device for Low Temperature Phosphorimetry, Applied Spectroscopy, vol. 34, No. 3, 1980, pp. 348–350.

Colmsjo, Anders & Ulf Stenberg, The Effect of n-Alkane Solvents on Low Temperature Quasilinear Fluorescence Spectra of Some Polyaromatic Hydrocarbons, Dept. of Analytical Chemistry, Univ. of Stockholm, 1976.

Reedy, Gerald T., Deon G. Ettinger, & John F. Schneider, High-Resolution Gas Chromatography/Matrix Isolation Infrared Spectrometry, Analytical Chemistry, vol. 57, No. 8, Jul. 1985, pp. 1602–1609.

Hauge, Robert H., Leif Fredin, Zakya H. Kafafi & John L. Margrave, A Multisurface Matrix-Isolation Apparatus, Applied Spectroscopy, vol. 40, No. 5, 1986, pp. 588–595.

Primary Examiner—Robert J. Warden
Assistant Examiner—Timothy M. McMahon
Attorney, Agent, or Firm—Dennis P. Clarke

[57] ABSTRACT

A method and apparatus for scientific analysis of a sample under low temperature vacuum conditions uses a vacuum chamber with a conveyor belt disposed therein. One end of the conveyor belt is a cool end in thermal contact with the cold stage of a refrigerator, whereas the other end of the conveyor belt is a warm end spaced from the refrigerator. A septum allows injection of a sample into the vacuum chamber on top of the conveyor belt for spectroscopic or other analysis. The sample freezes on the conveyor belt at the cold end. One or more windows in the vacuum chamber housing allow spectroscopic analysis of the sample. Following the spectroscopic analysis, the conveyor belt may be moved such that the sample moves toward the warm end of the conveyor belt where upon it evaporates, thereby cleaning the conveyor belt. Instead of injecting the sample by way of a septum and use of a syringe and needle, the present device may be used in series with capillary-column gas chromatography or micro-bore high performance liquid chromatography.

23 Claims, 7 Drawing Sheets

METHOD AND APPARATUS FOR SCIENTIFIC ANALYSIS UNDER LOW TEMPERATURE VACUUM CONDITIONS

BACKGROUND OF THE INVENTION

This invention relates to a method and apparatus for use in scientific analysis of a sample. More specifically, it relates to the analysis of a sample under low temperature vacuum conditions.

Various scientific analysis techniques require, or give improved results, when the sample which is to be tested is cooled to a low temperature and placed under vacuum conditions. For example, various spectroscopic techniques involve analysis of a sample at low temperatures. One type of low temperature spectroscopic technique involves molecular luminescence. Such molecular luminescence is best observed when the samples are brought to liquid nitrogen temperature or below. Additionally, if a sample contains aromatic compounds dissolved in a suitable n-alkane solvent, extremely narrow-banded "quasi-linear" fluorescence spectra may result. This phenomenon, called the Shpol'skii effect, has become a valuable tool for the qualitative determination of polynuclear aromatic hydrocarbons.

The use of the Shpol'skii effect in the quantitative determination of polynuclear aromatic hydrocarbons has developed over the last few years such that the effect has now become a relatively useful tool in analytical spectrometry. The technique has been applied to the identification and quantitation of polynuclear aromatic hydrocarbons in environmental samples such as coal liquids, automobile exhaust, and air-borne particulates.

A major consideration encountered in the design of Shpol'skii spectrometric systems is the choice of the device used to cool the sample, this consideration also applying to other low temperature spectroscopic techniques. Three methods are commonly used for cooling in connection with Shpol'skii spectrometric systems. A liquid sample held in a quartz tube cell may be immersed in a Dewar flask filled with a coolant, such as liquid nitrogen or liquid helium. A second technique involves cooling a sample by conduction from a metallic rod immersed in a liquid coolant. A third technique involves cooling the sample while it is in contact with the cold stage of a Joule-Thomson refrigerator. Each of the methods has drawbacks. The handling of liquid nitrogen or liquid helium can be expensive, time consuming, and tedious, usually involving the manipulation of cumbersome Dewar flasks. On the other hand, Joule-Thomson refrigerators are usually large and bulky and often require elaborate vacuum systems and expensive gas compressors. As the refrigerators avoid the need for a liquid coolant, they have still been relatively attractive as sample cooling systems.

An important disadvantage with the Joule-Thomson refrigerators is the long cool down time associated with them. On the average, these refrigerators can cool a sample holding device from room temperature to 15° K. in about one hour. Such a long cool down time makes the refrigerator arrangement impractical if each sample must be cooled separately. As a result, several designs allow deposition of more than one sample onto the cold stage at a time. When this is done, each sample must be moved individually onto the viewing position of the spectrometric system. At least two different techniques have been used for the deposit of more than one sample onto the cold stage.

A first approach is shown in U.S. Pat. No. 4,594,226 Reedy, this approach also being discussed in *Analytical Chemistry*, Volume 57, No. 8, July, 1985, "High-Resolution Gas Chromatography/Matrix Isolation Infrared Spectrometry" by Reedy et al., Pages 1602–1609. A sample is frozen onto a cold metal disk attached to the refrigerator cold stage. A double O-ring seal between the base of the refrigerator and the vacuum shroud allows the entire cryostat to rotate independently of the chamber. The sample, in the form of effluent from a gas chromatography column, is frozen onto the disk as it rotates. Three complete rotations of the cryostat may be achieved in order to provide six hours of sampling time. After this time, the cold stage must be heated to remove the collected samples and the entire sample collection process may be repeated.

A second approach for moving samples individually into the viewing system of a spectrometric system is disclosed in *Applied Spectroscopy*, Volume 40, No. 5, 1986, "A Multisurface Matrix-Isolation Apparatus" by Hauge et al. at Pages 588–595. This approach uses a sample holder which is rotated relative to the cold stage of a refrigerator. The sample holder is a hollow cylindrical metal block physically attached to the cold stage of the refrigerator by a flexible multi-leaf copper coil. Sixty (60) sample compartments are positioned around the cylinder in five rows. A particular row is chosen by moving the entire cryostat in the vertical direction. The sample within a particular row is chosen by turning the sample holder relative to the cold stage via a rotary vacuum feed-through. After the 60 samples are analyzed, the cold stage must be heated to remove them.

Although the prior techniques, such as the sample moving techniques discussed in detail above, are useful analytically, they still suffer from two significant disadvantages. First, both require that the entire cryostat be moved. As the cryostat is usually quite heavy and has several electrical connections and high pressure gas lines attached, this is often cumbersome. Accurate positioning of the cryostat requires expensive and elaborate mechanical devices. Secondly, both of the prior sample moving techniques significantly limit the sampling time between the heatings of the cold stage. When the sample holder is filled, and following the analysis of all of the samples, the apparatus is no longer available for analysis when the sample holder is cleaned by heating the cryostat. The "down time" during heating and re-cooling is significant.

OBJECTS AND SUMMARY OF THE INVENTION

Accordingly, it is a primary object of the present invention to provide a new and improved apparatus for subjecting samples to low temperature vacuum conditions.

A further object of the present invention is to provide a method for scientific analysis of a sample.

A more specific object of the present invention is to provide for low temperature analysis of samples without the need for repeatedly warming up and recooling the cold stage of a refrigerator.

Another object of the present invention is to provide for low temperature analysis of a sample without the need to move an entire cryostat.

Yet another object of the present invention is to provide for low temperature analysis of a sample wherein a sample holder is self-cleaning.

A still further object of the present invention is to provide for low temperature analysis of a sample without the need for handling liquid refrigerants, such as liquid nitrogen or liquid helium.

The above and other objects of the present invention which will be more apparent as the description proceeds are realized by an apparatus for placing a sample under low temperature vacuum conditions for scientific analysis. (As used herein, a "low temperature" shall refer to a temperature below 100° K.) The apparatus includes a vacuum chamber having a sample entrance port, a cooling means within the vacuum chamber, a sample holding means within the vacuum chamber and disposable such that the cooling means will cool a sample on the sample holding means to a given low temperature for analysis. The entrance port is operable to allow the transfer of a sample from outside the vacuum chamber to the sample holding means inside of the vacuum chamber while the vacuum chamber remains at vacuum and while the cooling means is at low temperature. The apparatus is operable to cause the evaporation of the sample from the sample holding means so as to clean the sample holding means while the vacuum chamber remains at vacuum and the cooling means is at low temperature. The sample holding means is more specifically a conveyor belt having a cool end adjacent to the cooling means and a warm end removed from the cooling means. The apparatus further includes a rotator to move the conveyor belt and the apparatus causes evaporation of the sample by the rotator moving the sample from the cool end towards the warm end. The cooling means is a refrigerator having a cold stage thermally coupled to the cool end and the refrigerator stays on when the sample is evaporated. Indeed, the refrigerator should be kept on all the time so that it will be ready to quickly freeze any samples placed on the belt. The entrance port is a septum which maintains the vacuum in the vacuum chamber and which is permeable by a needle to allow injection of a sample from a syringe. The apparatus may further include a chromatographic column mounted to the vacuum chamber for providing chromatographic separation of a sample before it is transferred to within the vacuum chamber. The rotator may be a motor or, alternately, may be a manually rotatable knob. The apparatus further includes means for performing analytical spectrometry analysis on a sample disposed on the sample holding means.

The method of the present invention involves the scientific analysis of a sample under low temperature vacuum conditions. The method includes the steps of evacuating a vacuum chamber, cooling a cooling means within the vacuum chamber, transferring a sample from outside of the vacuum chamber to a sample holding means inside of the vacuum chamber while the vacuum chamber is at vacuum and the cooling means is at operational low temperature, cooling the sample by having the cooling means cool the sample holding means, analyzing the sample when it has reached a given low temperature, and, after the analyzing step is complete, warming the sample such that it evaporates from the holding means so as to clean the sample holding means, the cooling means remaining at low temperature during the warming step. The cooling step is accomplished by a refrigerator which serves as the cooling means. The warming step is accomplished by moving at least a portion of the sample holding means away from the cooling means. The sample holding means is a conveyor belt and the warming step is accomplished by moving the conveyor belt such that the sample is moved away from the cooling means. The transferring step may be accomplished by use of a syringe. The analyzing step is an analytical spectrometry analysis. The method may further include the step of subjecting the sample to chromatographic separation before the transferring step, the chromatographic separation causing different constituents of the sample to be disposed on different parts of the conveyor belt and wherein the analyzing step involves analytical spectrometry analysis of each of the constituents. The conveyor belt is moved by operation of a motor. The conveyor belt may alternately be moved by operation of a manually rotatable knob.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
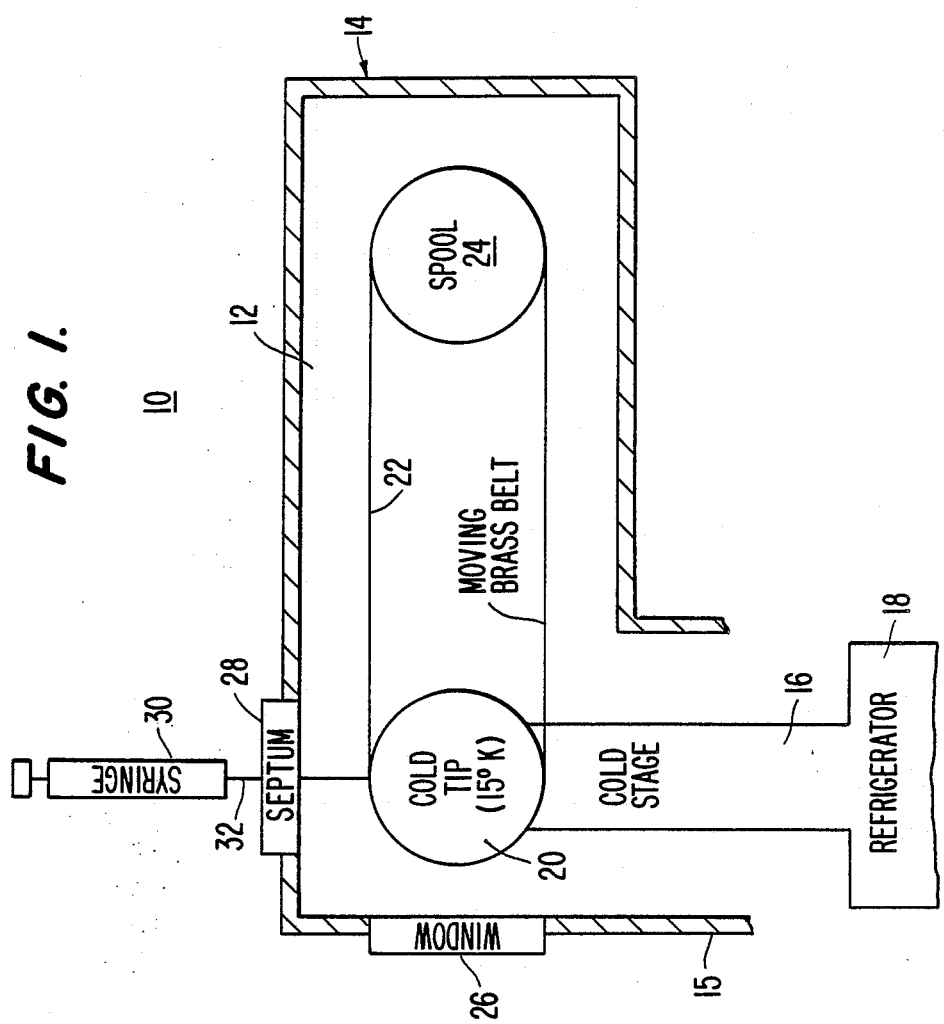
FIG. 1 shows a simplified side view of the present invention with a housing shown in cross-section and some parts partially shown and illustrated schematically.

The apparatus 10 of the present invention is depicted in simplified form in FIG. 1. The apparatus 10 includes a vacuum chamber 12 within a housing 14, the housing being only partially shown. A cold stage 16 of a refrigerator 18 extends into the vacuum chamber 12. A generally cylindrical portion 15 of the housing 14 may extend downwardly to an attachment to the base of refrigerator 18 by a double O-ring seal. The attachment and sealing arrangement are not shown as they are not central to the present invention and various well known attachment and sealing arrangements could be used. The refrigerator 18 is preferably a closed-cycle helium refrigerator that cools a copper cold tip to 11° K. in 45 minutes without the need for liquid helium. For example, the commercially available Displex Model CX-202 by Air Products Company of Allentown, PA could be used as the refrigerator 18.

A cold tip 20 is attached to the top of the cold stage or cooling rod 16 in a manner discussed below in connection with FIGS. 2 and 3. As shown, the cold tip 20 will be about 15° K. when the refrigerator 18 is turned on. Extending from the cold tip 20 is a brass conveyor belt 22 which also extends around a spool 24 shown schematically in FIG. 1. The brass belt 22 is preferably cut from a piece of 0.002 inches thick stock of brass and the piece has its ends spot-welded together so that the belt forms a continuous loop. The belt 22 is placed around the cold tip 20 and the spool 24 so that it is taut.

The conveyor belt 22 serves as a sample holding means to allow scientific analysis, such as analytical spectrometric analysis, of a sample under low temperature vacuum conditions by way of window 26. Window 26 and another window (not visible in FIG. 1) spaced 90° from the window 26 allow light to be transmitted into the vacuum chamber 12 and to be transmitted out of the vacuum chamber.

A septum 28 serves as an entrance port which allows insertion of a sample into the vacuum chamber 12 by way of syringe 30 and needle 32 even while the vacuum chamber 12 is at a vacuum and the refrigerator 18 is operational at low temperature. As shown, the septum or entrance port 28 is positioned directly over the cold tip 20. The septum 28 is preferably made of rubber.

Figure 2:
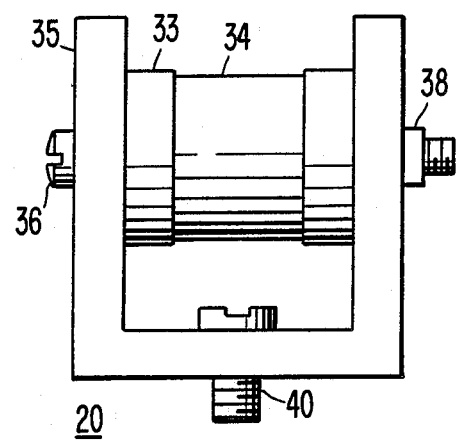
FIG. 2 shows a front view of a cold tip as used with the present invention.
Figure 3:
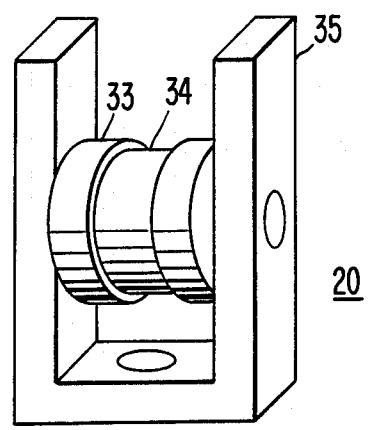
FIG. 3 shows a perspective view of the cold tip of the present invention.

As shown in FIGS. 2 and 3, the cold tip 20 includes a spool 33 having a groove 34 disposed therein. The spool 33 is held to a horseshoe-shaped frame 35 by a bolt 36 and nut 38. The spool 33 is stationary relative to the frame 35. A bolt 40 is used to hold the bottom (relative to FIG. 2) of the frame 35 to the cold stage 16 (cold stage 16 shown in FIG. 1 only). The bolts are not shown in FIG. 3 for ease of illustration. The cold tip 20 is made of oxygen-free high conductivity copper. The groove 34 is designed to be just wider than the width of the brass conveyor belt 22. The brass conveyor belt 22 (not shown in FIGS. 2 or 3) would be seated within the groove 34.

Figure 4:
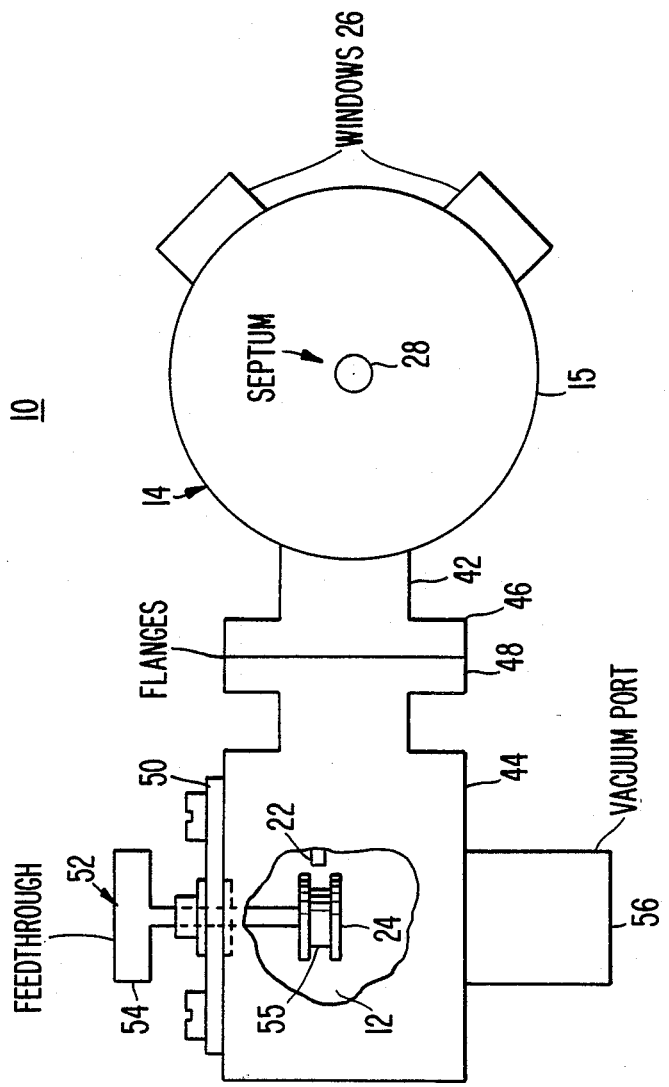
FIG. 4 shows a top view of the present invention with a portion of an upper wall broken away and with a portion of the conveyor belt broken away.

As shown in the top view of FIG. 4, the portion 15 of housing 14 is preferably a stainless steel pipe which is cylindrical and has a center axis extending vertically. The pipe 15 is attached to a horizontally extending portion 42 which connects to a hollow stainless steel block 44 by way of bolted together flanges 46 and 48. The interior of the block 44 will, of course, be a part of the vacuum chamber 12.

The block 44 has a plate 50 bolted to one side of it and upon which a rotary motion vacuum feed-through 52 is mounted. The feed-through 52 has a manually operable knob 54 which turns the interior plastic spool 24. The plastic spool 24 is grooved, in somewhat similar fashion to the groove 34 in copper spool 33 of FIGS. 2 and 3, and has a rubber lining 55 in the groove so as to supply adequate friction for moving the conveyor belt 22 to slide across the stationary copper spool 33 (spool 33 not shown in FIG. 4). A vacuum port 56 is mounted to the steel block 44 and would be used for connection to a vacuum pump (not shown) which would serve to evacuate the vacuum chamber 12.

The feed-through 52 serves as a rotator and may be a commercially available direct-drive rotary motion base plate feed-through such as Model BP-20.

Figure 5:
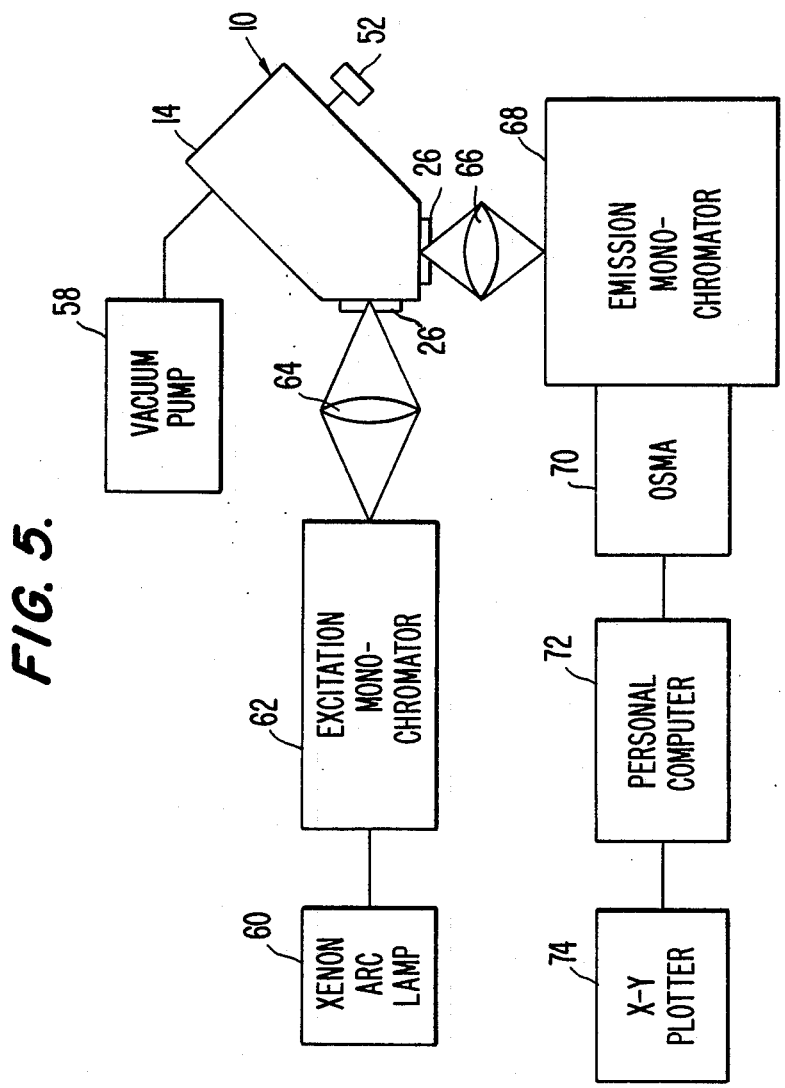
FIG. 5 is a block diagram illustrating the use of the present invention for a specific scientific analysis process.

FIG. 5 shows a block diagram of a particular spectrometric system using the apparatus 10 in conjunction with various commercially available components. A vacuum pump 58 is used to evacuate the interior of housing 14. A 150 watt Xenon Arc-lamp applies light through a Jobin-Yvon Model H.10 monochromator to select an excitation wavelength applied via lens 64 through one of the windows 26. A laser alternately could be used to provide the excitation radiation. The light will be focused upon a sample (not shown in FIG. 5) on the brass belt in contact with the cold tip inside of the housing 14. Florescence emitted from a sample on the belt is collected by lens 66 via the other window 26 and focused on the entrance slit of a 0.5 meter Spex Model 1870 Czerny-Turner spectrograph. Radiation flux at the exit port of the spectrograph or emission monochromator 68 is detected by an optical spectrometric multichannel analyzer (OSMA) such as Princeton Instrument's Model IRY-10246. The OSMA is a linear photo-diode array 2.56 millimeters long with 1024 elements. It is water-cooled to −24° C. and is positioned at the exit focal plane of the spectrograph. The array length corresponds to 40 nanometers in wavelength units. The detector 70 is interfaced with and controlled by a PCS Limited 286 Series personal computer 72 which supplies data for plotting by a Hewlitt-Packard Model 7440A Color Prographics Plotter.

OPERATION

The operation of the apparatus 10 will now be discussed with reference to FIGS. 1, 4, and 5 and based upon experience with an actual prototype. After the initial cooling down period of the refrigerator 18, the cold tip 20 is kept at 15° K. or below until completion of the experiment. Pressure inside the chamber is maintained at a vacuum of 3 mtorr. Sample injections may be made as follows. The excitation monochromator is set to a visible wavelength, usually green, so the cold tip may be viewed easily. Depending upon the relative location between the lenses 64 and 66 and windows 26 (FIG. 5), a small dental mirror may be used to see inside the vacuum chamber through one of the windows. A disposable 1.0 milliliter syringe 30 with a three inch needle 32 is filled to the 50 microliter mark. The needle is easily passed through the septum 28 until the tip of the needle rests against the brass conveyor belt in contact with the cold tip (as seen in FIG. 1) the sample is injected slowly so that a single 50 microliter drop forms on the belt. An initial rise in temperature may occur on the cold tip, for example to about 25° K. or 30° K. After about two minutes, the cold tip has again reached a temperature at or below 15° K. Next, the belt is moved via the rotary motion feedthrough 52 so that the image of the green excitation light covers the injection sample.

Once the sample is in place, the appropriate excitation wavelength is chosen. The sample is illuminated using an 8 nanometer excitation monochromator band pass. Likewise, the appropriate emission wavelength range is selected. The band pass of the emission monochromator is 0.4 nanometers. An emission spectrum of the sample is taken and stored in the computer 72. After the spectrum is stored, the conveyor belt 22 is moved by turning knob 52 so that the portion having the sample frozen thereon is no longer in contact with the cold tip. The sample quickly warms as it moves from the cold end corresponding to cold tip 20 towards the warm end of the belt 22 corresponding to spool 24. As the sample warms, it evaporates and is pumped away by the vacuum pumping system. Another injection may be made immediately.

Most importantly, samples may be repeatedly injected or transferred into the vacuum chamber 12 without the need for turning off or otherwise warming up the refrigerator 18. Advantageously, the moving brass belt 22 operates as a self-cleaning sample holder. The apparatus 10 may be repeatedly used for different samples without the need to turn off the refrigerator 18 or allow pressure into the vacuum chamber 12.

Depending upon the specific type of scientific analysis, such as a spectrometric analysis, three or more injections of each sample might be used to provide an average. Calibration curves from the plotter 74 would normally be plotted in terms of height versus concentration.

In addition to the low temperature spectroscopic technique described above, the apparatus 10 would be useful for numerous other scientific analysis techniques. Among these techniques are laser excited molecular luminescence spectrometry with gated detection, low temperature Fourier transform infrared absorption spectrometry, low temperature UV-VIS molecular absorption spectrometry and low temperature Raman spectrometry. The device can be applied to sampling techniques or methods such as matrix isolation and Shpol'skii spectrometry.

APPARATUS AND METHOD WITH CHROMATOGRAPHIC TECHNIQUES

Figure 6:
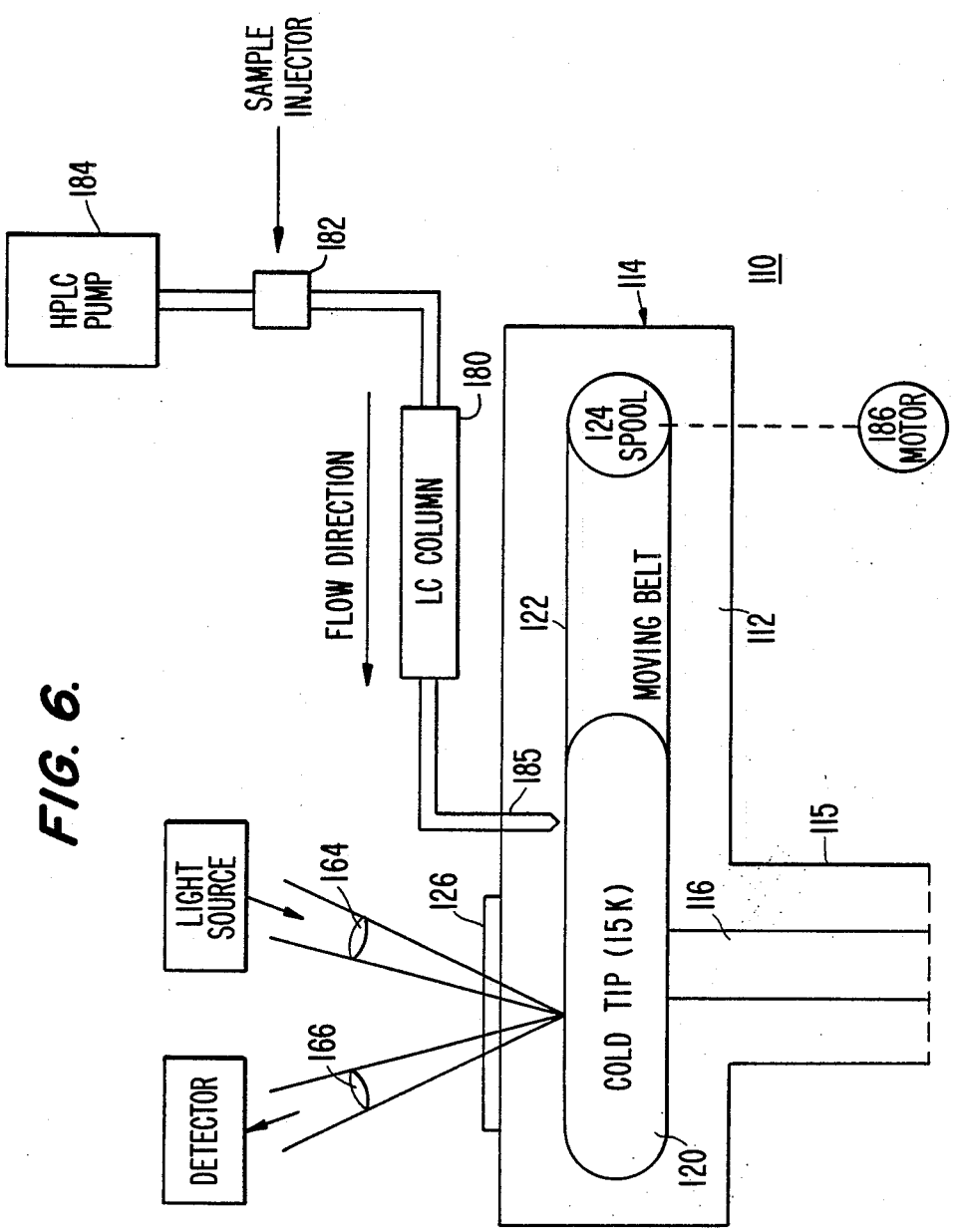
FIG. 6 shows a simplified side view with most parts represented schematically of a second embodiment of the present invention.

FIG. 6 shows an embodiment 110 of the present invention wherein chromatographic techniques are combined with the spectroscopic techniques. The components of FIG. 6 are in the "100" series with the same last two digits as the corresponding component, if any, of the embodiment of FIGS. 1-5. Accordingly, the discussion of the apparatus 110 will concentrate upon differences between it and the apparatus 10.

The apparatus 110 has a vacuum chamber 112 within a housing 114 which also houses the cold stage 116 of a refrigerator (only the cold stage 116 is shown). A cold tip 120 is used to support a brass conveyor belt 122 also coupled to plastic spool 124. The cold tip 120 is larger than the cold tip 20 described above. Essentially, the cold tip 120 is constructed in similar fashion to the cold tip 20 of FIGS. 2 and 3 except that the cold tip 120 has the shape illustrated in the side view of FIG. 6, instead of a circular side profile as for the spool 33 of FIGS. 2 and 3. By making the spool of cold tip 120 larger in the discussed manner and the frame larger (not shown in FIG. 6) to extend further in a right to left direction in FIG. 6, the belt 122 remains cold over a larger portion of its travel.

A liquid chromatographic column 180 is supplied via a sample injector 182 connected to pump 184. The arrangement provides for chromatographic separation of constituents within a sample prior to their injection onto the conveyor belt 122 by use of known techniques for supplying the output of a chromatographic column such as 180 to a vacuum chamber 112. The column 180 is connected to the vacuum chamber 112 by way of an entrance port 185 which allows the sample to be transferred into the vacuum chamber 112 without the vacuum chamber 112 losing its vacuum. Likewise, the samples can be transferred to within the chamber 112 while the cold stage 116 of the refrigerator is operating and remains at a cold temperature.

The spool 124 would be constructed in essentially identical fashion to the spool 24 discussed in detail above. However, a motor 186 such as a stepping motor may be connected to the spool 184 to serve as a rotator for moving the belt 122. The motor 186 would be connected to the spool 124 in similar fashion to the connection between the manual knob 52 (refer back momentarily to FIG. 4) and the spool 24. The motor is used to insure that different constituents of a sample fall on different parts of belt 122.

The housing 114 of the apparatus 110 is somewhat different in shape as shown at the left side of FIG. 6 than the housing 14 of apparatus 10. Additionally, a single window 126 may be mounted upon the top of the housing 114 and used for both supplying light to the sample via lens 164 and receiving light from the sample via lens 166.

Figure 7:
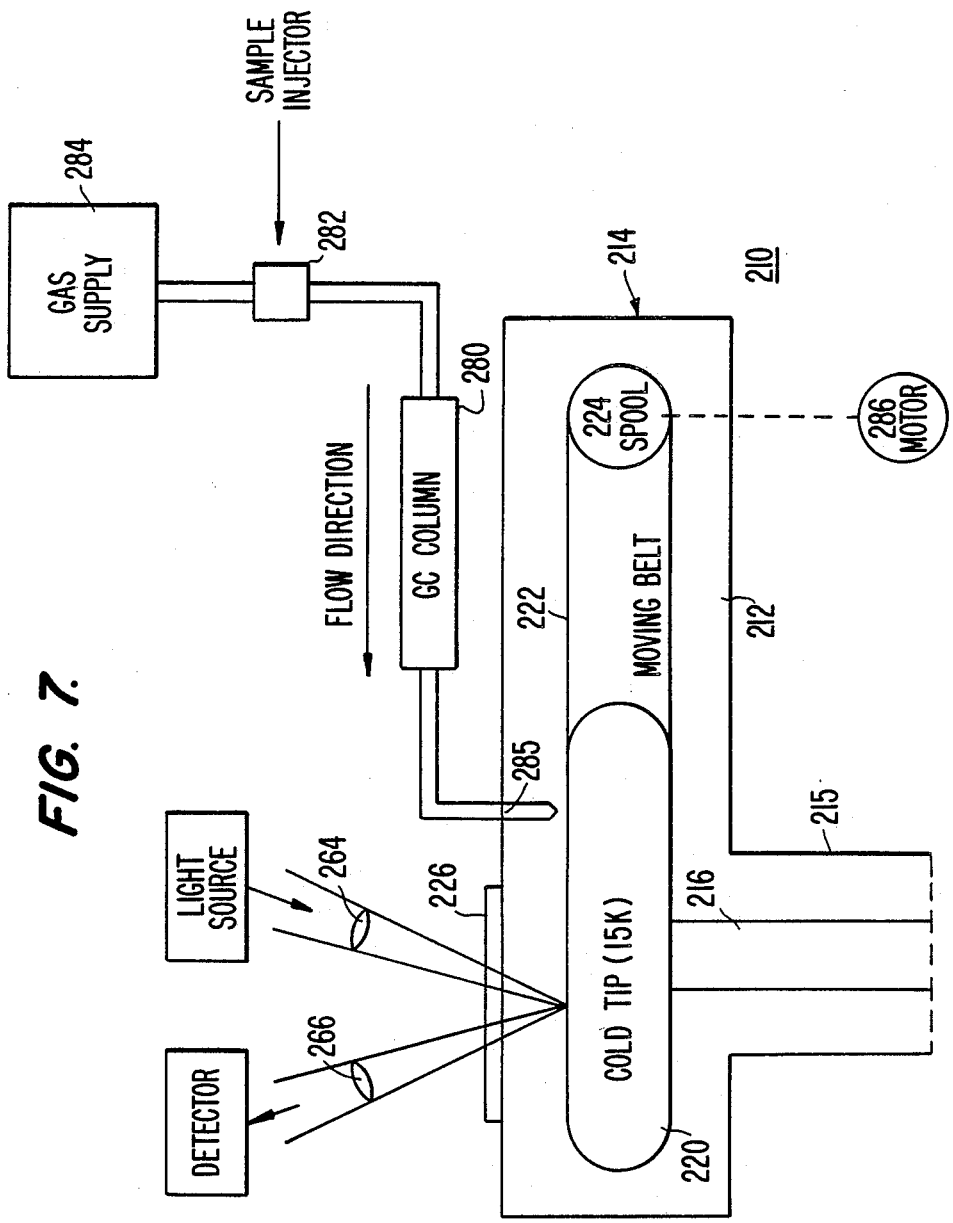
FIG. 7 shows a simplified side view with most parts represented schematically of a third embodiment of the present invention.

FIG. 7 shows an embodiment essentially similar to FIG. 6 except that a gas chromatographic column 280 is used. Additionally, a gas supply 284 is used in conjunction with sample injector 282. The arrangement of FIG. 7 will provide gas chromatographic separation prior to the spectroscopic analysis by way of the lenses 264 and 266. The apparatus 210 of FIG. 7 has components labeled in the "200" series with the same last two digits as the corresponding component in the previous embodiments. Accordingly, these components need only be briefly mentioned. The vacuum chamber 212 has a housing 214 including a portion 215. A refrigerator cold stage 216 has a cold tip 220 attached to its top. A moving brass conveyor belt 222 extends between the cold tip 220 and a spool 224 which may be operated by a stepping motor 286. An entrance port 285 is used to supply a sample from the column 280.

Figure 8:
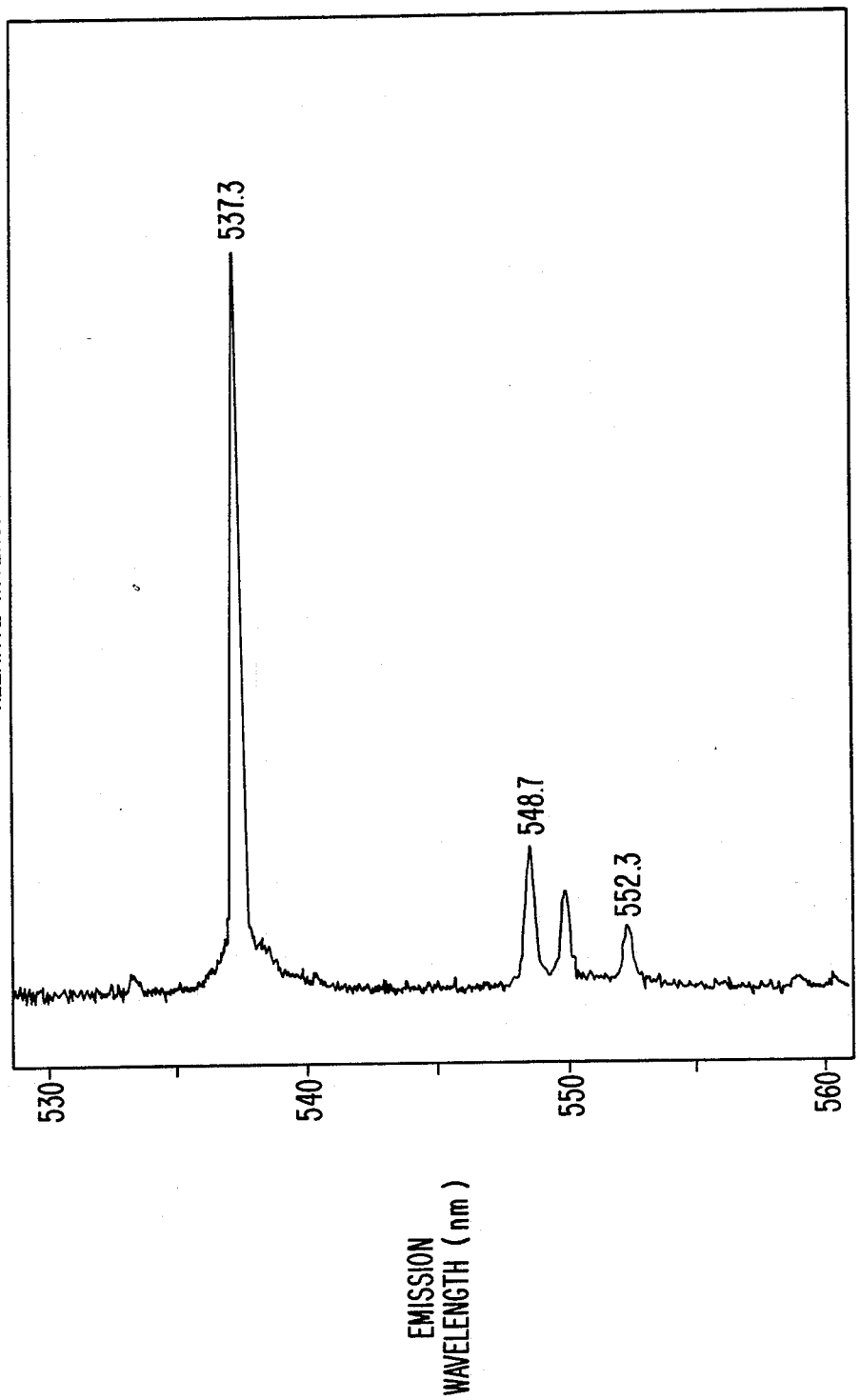
FIG. 8 shows a spectrum which was obtained by use of the present invention.

FIG. 8 shows the phosphorescence spectrum of 150 ng 1,2-Benzopyrene in 50 microliters of hexane at 15° K. and is illustrative of the type of output information which can be obtained with the use of the present apparatus.

The apparatus of the present invention is especially advantageous in that it is self-cleaning so that the refrigerator never needs to be warmed to room temperature. As a result, samples can be run continuously, requiring only five minutes or less for each sample.

The present apparatus is further advantageous in that the device includes a relatively low number of moving parts. Only the brass conveyor belt, the plastic spool, and the feed-through mechanism move. The refrigerator itself is stationary so that it is unnecessary to move the relatively heavy refrigerator. Also, the present system avoids the use of liquid coolant and the temperatures may be set anywhere in the range of 11° K.-300° K. using a small internal electric heater such as that provided in the specified model refrigerator discussed above.

When using the present invention, care must be taken to obtain reproducible injection samples. If the injected droplet is at a different site and shape each time, precision problems may be caused. However, reproducibility of the injection of the sample may be improved by the use of a commercially available specialized syringe that has a precision of 1% for successive injection and which delivers samples at a constant rate.

Although various specific constructions have been discussed herein, it is to be understood that these are for illustrative purposes only. Various modifications and adaptations will be readily apparent to those of skill in the art. Accordingly, the present invention should be determined by the reference to the claims appended hereto.

What is claimed is:

1. A method of scientific analysis of a sample under low temperature vacuum conditions, the steps comprising:

evacuating a vacuum chamber;

cooling a cooling means within the vacuum chamber;

transferring the sample from outside of a vacuum chamber to a sample holding means inside of the vacuum chamber while the vacuum chamber is at vacuum and the cooling means is at low temperature;

cooling the sample by having the cooling means cool the sample holding means;

analyzing the sample when it has reached a given low temperature; and after the analyzing step is complete, warming the sample such that it evaporates from the sample holding means so as to clean the sample holding means, the cooling means remaining at low temperature during the warming step wherein said warming step is accomplished by separating at least a portion of the sample holding means from the cooling means.

2. The method of claim 1 wherein said cooling step is accomplished by a refrigerator which serves as the cooling means.

3. The method of claim 2 wherein said warming step is accomplished by moving at least a portion of the sample holding means away from the cooling means.

4. The method of claim 3 wherein the sample holding means is a conveyor belt and said warming step is accomplished by moving the conveyor belt such that the sample is moved away from the cooling means.

5. The method of claim 4 wherein said transferring step is accomplished by use of a syringe.

6. The method of claim 5 wherein said analyzing step is an analytical spectrometry analysis.

7. The method of claim 4 wherein said analyzing step is an analytical spectrometry analysis.

8. The method of claim 7 further comprising the step of subjecting the sample to chromatographic separation before said transferring step, the chromatographic separation causing different constituents of the sample to be disposed on different parts of the conveyor belt and wherein said analyzing step involves analytical spectrometry analysis of each of the constituents.

9. The method of claim 8 wherein the conveyor belt is moved by operation of a motor.

10. The method of claim 4 wherein the conveyor belt is moved by operation of a manually rotatable knob.

11. An apparatus for placing a sample under low temperature vacuum conditions for scientific analysis comprising:

a vacuum chamber having an entrance port;

a cooling means within the vacuum chamber; a sample holding means within the vacuum chamber and disposed such that the cooling means will cool a sample on said sample holding means to a given low temperature for analysis; and wherein said entrance port is operable to allow the transfer of a sample from outside said vacuum chamber to said sample holding means inside of said vacuum chamber while the vacuum chamber remains at vacuum and said cooling means is at low temperature, and wherein said apparatus is operable to cause the evaporation of the sample from said sample holding means so as to clean said sample holding means while the vacuum chamber remains at vacuum and said cooling means is at operational low temperature wherein said sample holding means is a conveyor belt having a cool end adjacent to said cooling means and a warm end removed from said cooling means.

12. The apparatus of claim 11 further including a rotator to move said conveyor belt and wherein said apparatus is operable to cause the evaporation of a sample by said rotator moving the sample from the cool end towards the warm end.

13. The apparatus of claim 12 wherein said cooling means is a refrigerator having a cold stage thermally coupled to said cool end.

14. The apparatus of claim 13 wherein said entrance port is a septum which maintains the vacuum in said vacuum chamber and which is permeable by a needle to allow injection of a sample from a syringe.

15. The apparatus of claim 13 further comprising a chromatographic column mounted to said vacuum chamber for providing chromatographic separation of a sample before it is transferred to within said vacuum chamber.

16. The apparatus of claim 15 wherein said rotator is a motor.

17. The apparatus of claim 12 wherein said rotator is a manually rotatable knob.

18. The apparatus of claim 11 further comprising means for performing analytical spectrometry analysis on a sample disposed on said sample holding means.

19. An apparatus for placing a sample under low temperature vacuum conditions for scientific analysis comprising:

a vacuum chamber having an entrance port to allow placement of a sample therein;

a cooling means within the vacuum chamber;

a conveyor belt within the vacuum chamber and having a cool end adjacent to said cooling means and a warm end removed from said cooling means; and a rotator for moving said conveyor belt; and wherein the apparatus is operable to cool a sample placed at said cool end of said conveyor belt for analysis and said rotator is operable to move the sample towards said warm end of said conveyor belt such that the sample evaporates.

20. The apparatus of claim 19 wherein said entrance port is operable to allow a sample to be placed in said vacuum chamber when said vacuum chamber is at vacuum and said cooling means is at low temperature.

21. The apparatus of claim 20 wherein said cooling means is a refrigerator.

22. The apparatus of claim 20 further comprising means for performing analytical spectrometry analysis on a sample on said conveyor belt.

23. The apparatus of claim 20 wherein said entrance port is a septum.

* * * * *

UNITED STATES PATENT AND TRADEMARK OFFICE
CERTIFICATE OF CORRECTION

PATENT NO. : 4,942,134
DATED : July 17, 1990
INVENTOR(S) : James D. WINEFORDNER, ET AL It is certified that error appears in the above-identified patent and that said Letters Patent is hereby corrected as shown below:

In column 1, under the title of the invention, please add the following after line 5:

-- Research leading to the completion and reduction to practice of the invention was supported, in part, by Grant No. GM-11373-23 issued by the National Institutes of Health (NIH) and Grant No. DEA-S05780R06022 issued by the Department of Energy (DOE). The United States Government has certain rights in and to the claimed invention. --

Signed and Sealed this

Thirtieth Day of November, 1993

Attest:

BRUCE LEHMAN

*Attesting Officer*  *Commissioner of Patents and Trademarks*